United States Patent
Harding et al.

(10) Patent No.: US 11,406,810 B2
(45) Date of Patent: Aug. 9, 2022

(54) SYSTEMS AND METHODS OF FACILITATING INSTRUMENT DELIVERY TO A CATHETER ASSEMBLY

(71) Applicant: Becton, Dickinson and Company, Franklin Lakes, NJ (US)

(72) Inventors: Weston Harding, Lehi, UT (US); Jonathan Karl Burkholz, Salt Lake City, UT (US); Curtis H Blanchard, Riverton, UT (US); John Cendagorta, Draper, UT (US); Austin Jason McKinnon, Herriman, UT (US); Joseph Spataro, Cottonwood Heights, UT (US); Cristian Clavijo, Lehi, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 353 days.

(21) Appl. No.: 16/551,345

(22) Filed: Aug. 26, 2019

(65) Prior Publication Data

US 2020/0078579 A1 Mar. 12, 2020

Related U.S. Application Data

(60) Provisional application No. 62/729,310, filed on Sep. 10, 2018.

(51) Int. Cl.
*A61M 39/10* (2006.01)
*A61M 25/09* (2006.01)
*A61M 39/00* (2006.01)

(52) U.S. Cl.
CPC .... *A61M 39/105* (2013.01); *A61M 25/09041* (2013.01); *A61M 2039/0018* (2013.01);
(Continued)

(58) Field of Classification Search
CPC .......... A61M 39/105; A61M 25/09041; A61M 2039/0018; A61M 2039/1077; A61M 2205/0222; A61M 2039/1072; A61M 39/06; A61M 25/0606; A61M 2039/066; A61M 25/0097; A61M 25/0637; A61M 25/0693; A61M 2039/0081;
(Continued)

(56) References Cited

U.S. PATENT DOCUMENTS 6,363,273 B1   3/2002  Mastrorio et al.
10,543,354 B2*  1/2020  Bihlmaier ............. A61M 39/16
(Continued)

FOREIGN PATENT DOCUMENTS

WO    2016/036468    3/2016

*Primary Examiner* — Nilay J Shah
*Assistant Examiner* — Robert F Allen
(74) *Attorney, Agent, or Firm* — Kirton McConkie; Whitney Blair; Kevin Stinger

(57) ABSTRACT

A catheter adapter may include a distal end, a proximal end, a lumen extending between the distal end and the proximal end, and a side port. A central axis of a fluid path extending through the side port may be disposed at an angle with respect to a longitudinal axis of the catheter adapter. The angle may be less than 45°. Additionally or alternatively to the angle being less than 45°, the catheter adapter may include a wedge and/or an insert configured to facilitate instrument delivery to the catheter assembly via the side port.

17 Claims, 18 Drawing Sheets

(52) U.S. Cl.
CPC .............. *A61M 2039/1072* (2013.01); *A61M 2039/1077* (2013.01); *A61M 2205/0222* (2013.01)

(58) Field of Classification Search
CPC .. A61M 2039/0294; A61M 2039/0235; A61M 25/0029; A61M 2039/0226; A61M 25/0026; A61M 2025/0681; A61M 39/26
See application file for complete search history.

(56) References Cited

U.S. PATENT DOCUMENTS

| | | | |
|---|---|---|---|
| 2007/0088253 A1 | 4/2007 | Yacoubian et al. | |
| 2008/0082051 A1* | 4/2008 | Miller | A61M 25/09041 604/164.13 |
| 2013/0138080 A1* | 5/2013 | Andino | A61M 25/0015 604/508 |
| 2013/0237925 A1 | 9/2013 | Trainer et al. | |
| 2017/0043101 A1* | 2/2017 | Cole | A61M 5/3287 |
| 2017/0120034 A1* | 5/2017 | Kaczorowski | A61M 39/1055 |
| 2017/0326340 A1* | 11/2017 | Howell | A61M 25/02 |
| 2017/0348510 A1* | 12/2017 | Shevgoor | A61L 29/14 |
| 2018/0256857 A1* | 9/2018 | Naing | A61M 25/0631 |
| 2019/0022357 A1 | 1/2019 | Burkholz et al. | |
| 2019/0366052 A1* | 12/2019 | Burkholz | A61M 25/0029 |

\* cited by examiner

SYSTEMS AND METHODS OF FACILITATING INSTRUMENT DELIVERY TO A CATHETER ASSEMBLY

RELATED APPLICATIONS

This application claims the benefit of U.S. Provisional Application No. 62/729,310, filed Sep. 10, 2018, and entitled SYSTEMS AND METHODS OF FACILITATING INSTRUMENT DELIVERY TO A CATHETER ASSEMBLY, which is incorporated herein in its entirety.

BACKGROUND

Catheters are commonly used for a variety of infusion therapies. For example, catheters may be used for infusing fluids, such as normal saline solution, various medicaments, and total parenteral nutrition, into a patient. Catheters may also be used for withdrawing blood from the patient.

A common type of catheter is an over-the-needle peripheral intravenous catheter ("PIVC"). As its name implies, the over-the-needle PIVC may be mounted over an introducer needle having a sharp distal tip. The PIVC and the introducer needle may be assembled so that the distal tip of the introducer needle extends beyond the distal tip of the PIVC with the bevel of the needle facing up away from skin of the patient. The PIVC and introducer needle are generally inserted at a shallow angle through the skin into vasculature of the patient.

In order to verify proper placement of the introducer needle and/or the PIVC in the blood vessel, a clinician generally confirms that there is "flashback" of blood in a flashback chamber of a PIVC assembly. Once placement of the needle has been confirmed, the clinician may temporarily occlude flow in the vasculature and remove the introducer needle, leaving the PIVC in place for future blood withdrawal and/or fluid infusion. The PIVC assembly may be coupled with an extension set, which may allow coupling of an infusion or blood withdrawal device at a location removed from an insertion site of the PIVC.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure relates generally to vascular access devices and related systems and methods. In some embodiments, a catheter assembly may include a distal end, a proximal end, a lumen extending between the distal end and the proximal end, and a side port. In some embodiments, a central axis of a fluid path extending through the side port may be disposed at an angle with respect to a longitudinal axis of the catheter adapter. In some embodiments, the angle may be less than 45°. In some embodiments, the angle may be about 25°.

In some embodiments, the catheter assembly may include a catheter, which may extend distally from the catheter adapter. In some embodiments, the catheter may include a PIVC. In some embodiments, a proximal end of the catheter may be glued within a distal end of the catheter adapter. In some embodiments, the catheter assembly may include a wedge disposed within the lumen of the catheter adapter. In some embodiments, the wedge may secure a catheter of the catheter assembly.

In some embodiments, the catheter assembly may include an insert proximate the wedge. In some embodiments, the insert and/or the wedge may be configured to guide an instrument moving from the side port distally through the catheter adapter. In some embodiments, the insert may be constructed of a rigid or semi-rigid material or another suitable material. In some embodiments, the wedge may be constructed of metal or another suitable material. In some embodiments, an inner surface of the wedge and/or the insert may include a lubricant.

In some embodiments, the insert may include a groove, which may extend along an entire length of the insert. In some embodiments, the groove may be aligned with the side port fluid path such that fluid may flow from the side port fluid path distally through the insert. In some embodiments, the wedge may include a mouth, which may include a shape of a truncated cone. In some embodiments, the wedge may include a stem proximate the mouth.

In some embodiments, a distal end of the insert may include a tapered portion that may contact an inner surface of the mouth. In some embodiments, a portion of the groove disposed proximate the stem and aligned with a central axis of the stem may include an inner diameter less than or equal to an inner diameter of the stem.

In some embodiments, the catheter assembly may include a septum disposed within the lumen of the catheter adapter. In some embodiments, the septum may include a guide portion to direct movement of the instrument as the instrument is advanced distally from the side port through the catheter adapter.

In some embodiments, the wedge may include another groove proximate a tunnel. In some embodiments, the other groove may be aligned with the side port fluid path such that fluid may flow from the side port fluid path distally through the groove and into the tunnel.

In some embodiments, the wedge may be disposed within the lumen of the catheter adapter. In some embodiments, the wedge may be disposed within a distal end of the catheter adapter such than the instrument advanced distally from the side port through the catheter adapter contacts an inner surface of a body of the catheter adapter prior to contacting the wedge.

In some embodiments, the wedge may be disposed within a distal end of the catheter adapter such than the instrument advanced distally from the side port through the catheter adapter contacts the inner surface of the body of the catheter adapter prior to contacting the wedge. In some embodiments, the wedge may be configured such that the instrument advanced distally from the side port through the catheter adapter contacts an inner surface of the stem without contacting an inner surface of the mouth.

In some embodiments, the inner surface of the mouth may be angled between about 60° and about 90° with respect to the longitudinal axis. In some embodiments, the instrument advanced distally from the side port through the catheter adapter may contact an inner surface of a first side of the mouth closer to the side port without or prior to contacting a side of the mouth opposite the first side.

In some embodiments, the catheter assembly may include the instrument. In some embodiments, the instrument may include an additional catheter or tube for fluid infusion or blood draw, a guidewire, a probe with a sensor, or a light tube for disinfection. In some embodiments, the instrument may include the tube and a guidewire may extend through the tube.

In some embodiments, the catheter assembly may include a platform protruding from a bottom of the catheter adapter and configured to contact skin of a patient. In some embodiments, the platform may be angled at about 6° with respect to the longitudinal axis.

In some embodiments, a bottom of the catheter adapter may include a securement platform configured to contact skin of a patient. In some embodiments, the securement platform may include a groove, at least a portion of which may be aligned with the longitudinal axis. In some embodiments, the groove may extend through the securement platform.

It is to be understood that both the foregoing general description and the following detailed description are exemplary and explanatory and are not restrictive of the invention, as claimed. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which.

DESCRIPTION OF EMBODIMENTS

Figure 1:
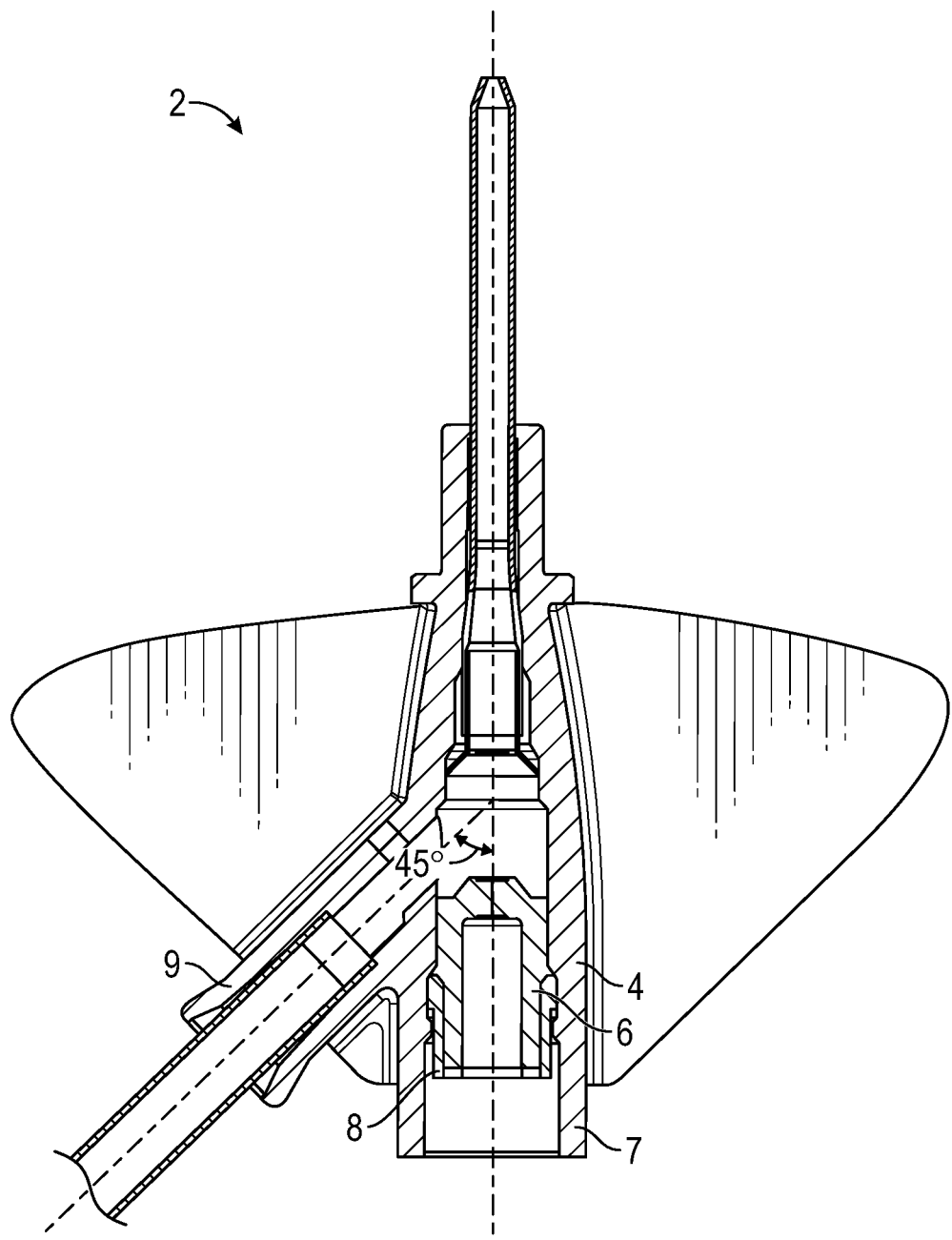
FIG. 1 is a cross-sectional view of a portion of a prior art catheter assembly.

Referring now to FIG. 1, a portion of a prior art catheter assembly 2 is illustrated. The prior art catheter assembly 2 may include or correspond to a catheter assembly of one or more of the following: the BD NEXIVA™ Closed IV Catheter System, the BD NEXIVA™ DIFFUSICS™ Closed IV Catheter System, or the BD PEGASUS™ Safety Closed IV Catheter System.

A catheter adapter 4 of the prior art catheter assembly 2 includes a septum 6. The septum 6 is at least partially disposed within a septum housing 8, which may include a canister. In some embodiments, the septum housing 8 prevents dislodgement or destabilization of the septum 6, thereby preventing leakage of fluid from the catheter adapter 4. An introducer needle may penetrate the septum 6, but the septum 6 seals a proximal end 7 of the catheter adapter 4 to fluid, which may instead enter a lumen of the catheter adapter 4 via a side port 9. The side port 9 and/or a fluid path extending through the side port 9 may be positioned at 45° to a longitudinal axis of the catheter adapter 4.

Figure 2A:
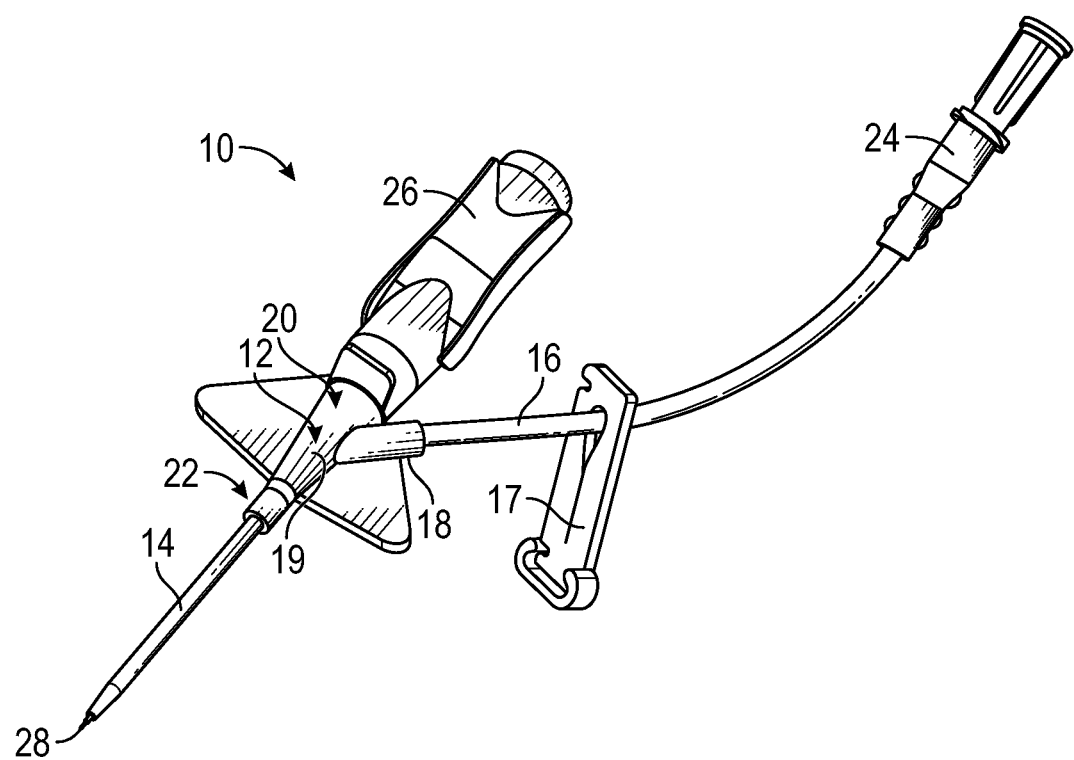
FIG. 2A is an upper perspective view of an example catheter assembly, according to some embodiments.
Figure 2B:
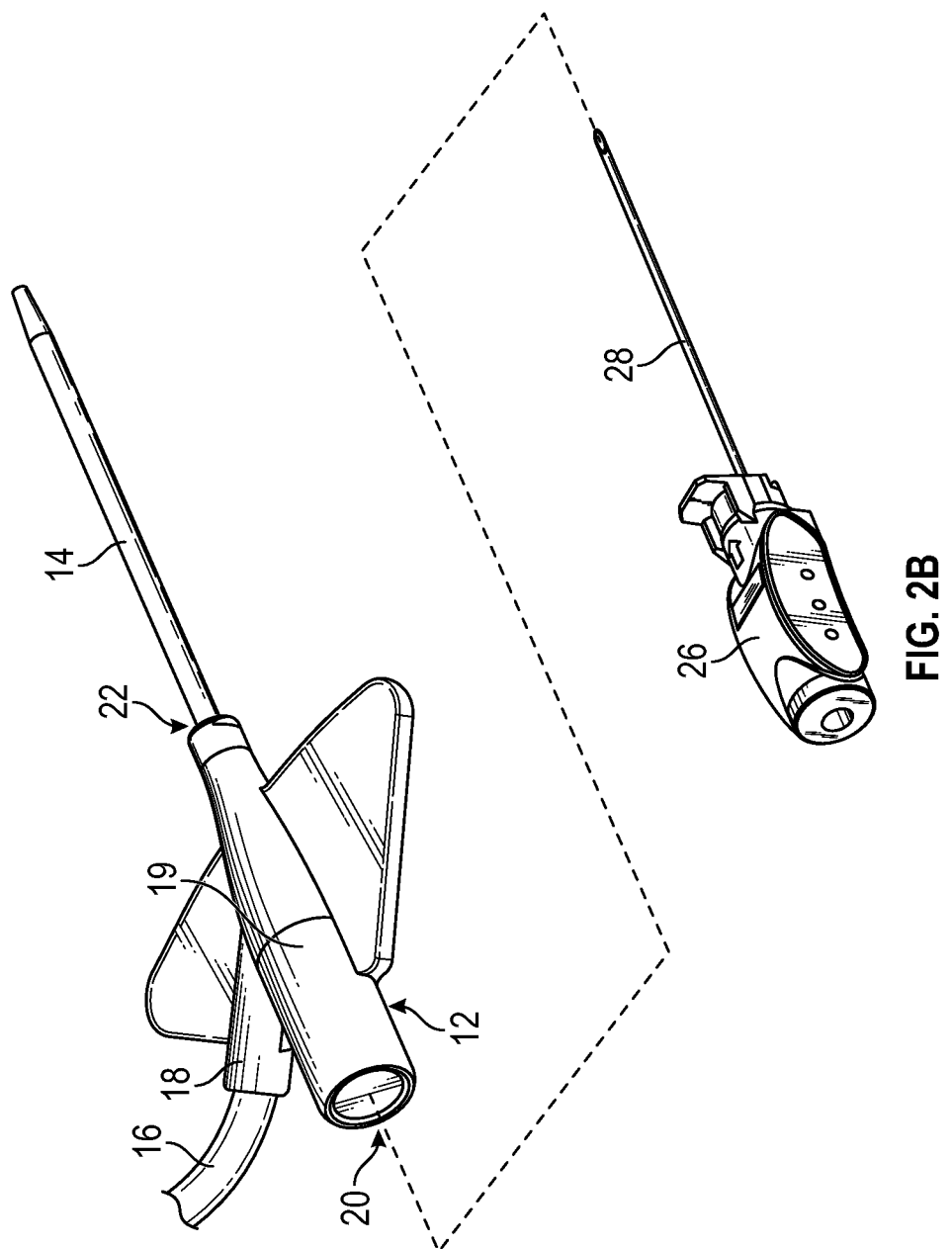
FIG. 2B is an upper perspective view of an example needle assembly removed from the catheter assembly of FIG. 2A, according to some embodiments.

Referring now to FIGS. 2A-2B, in some embodiments, a catheter assembly 10 may include a catheter adapter 12, a catheter 14 extending distally from the catheter adapter 12, and an extension tube 16 extending from the catheter adapter 12. In some embodiments, the catheter adapter 12 may include a side port 18, which may extend from a body 19 of the catheter adapter 12. In some embodiments, the extension tube 16 may extend from the side port 18. In some embodiments, the catheter adapter 12 may include a proximal end 20, a distal end 22, and a lumen extending therebetween. In some embodiments, the catheter 14 may include a peripheral intravenous catheter ("PIVC"). In some embodiments, the catheter assembly 10 may include one or more features of the prior art catheter assembly 2, such as, for example, the septum 6.

In some embodiments, the catheter assembly 10 may include a connector 24, which may be coupled to the extension tube 16. In some embodiments, the connector 24 may be configured to couple the catheter assembly 10 with a fluid infusion and/or blood withdrawal device. In some embodiments, the extension tube 16 may include a clamp 17, which may selectively close off the extension tube 16 to prevent blood or another fluid from flowing through the extension tube 16.

In some embodiments, the catheter assembly 10 may be removably coupled to a needle assembly, which may include a needle hub 26 and an introducer needle 28. In some embodiments, in response to the introducer needle 28 being inserted into a vein of the patient, flashback of blood may flow through a sharp distal tip of the introducer needle 28 and may be visible to a clinician between the introducer needle 28 and the catheter 14 and/or at another location within the catheter assembly 10.

In some embodiments, in response to confirmation via the blood flashback that the catheter 14 is positioned within vasculature of the patient, the needle assembly may be removed from the catheter assembly 10. In some embodiments, when the needle assembly is coupled to the catheter assembly 10, the introducer needle 28 of the needle assembly may extend through a septum disposed within the lumen of the catheter adapter 12.

Figure 2C:
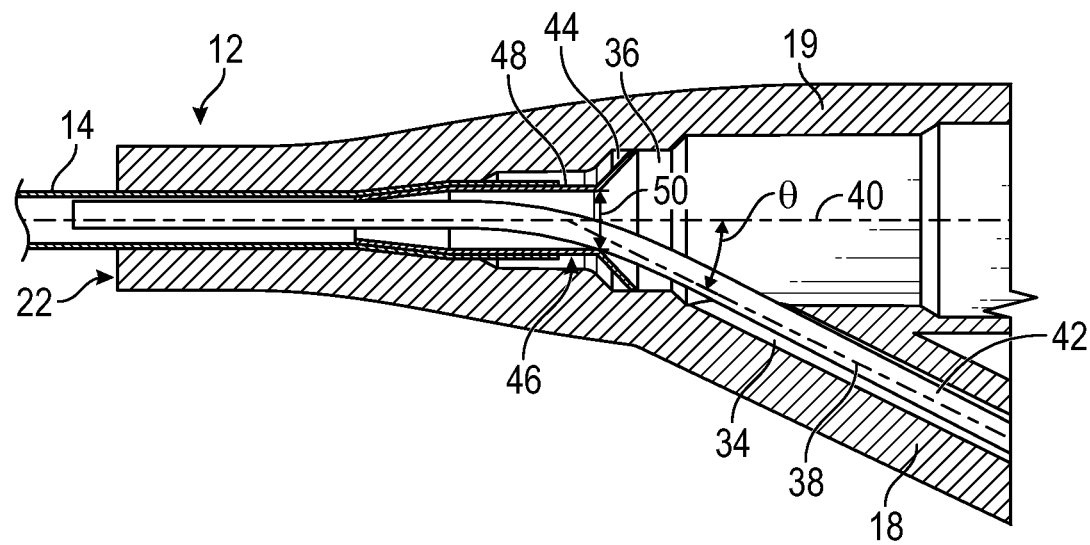
FIG. 2C is a cross-sectional view of an example wedge of the catheter assembly of FIG. 2A, according to some embodiments.

Referring now to FIG. 2C, in some embodiments, a side port fluid path 34, or a fluid path extending through the side port 18, may be disposed at an angle θ with respect to a body fluid path 36, or a fluid path of the body 19. In further detail, in some embodiments, a central axis 38 of the side port fluid path 34 may be disposed at the angle θ with respect to a central axis of the body fluid path 36, which may be aligned with a longitudinal axis 40 of the catheter adapter 12. In some embodiments, the angle θ may be less than 45°. In some embodiments, the angle θ may be between about 15° and about 35°. In some embodiments, the angle θ may about 25°. In some embodiments, the angle θ may be between about 10° and about 25°.

In some embodiments, an instrument 42 may be delivered to the vasculature of the patient via the side port fluid path 34 and the body fluid path 36. In some embodiments, the instrument 42 may include an additional catheter for fluid infusion or blood draw, a guidewire, a probe with a sensor, or a light tube for disinfection. In these embodiments, the instrument 42 may be advanced distally from the side port fluid path 34 to the body fluid path 36 and through the catheter 14, and the angle θ may facilitate advancement of the instrument 42. In some embodiments, the clinician may advance the instrument 42 distally from the side port fluid path 34 to the body fluid path 36 and through the catheter 14 when the catheter 14 is indwelling within the vasculature of the patient. Thus, minimal movement or disruption of the catheter assembly 10 may be desired.

If the angle θ were 45°, as illustrated in the prior art catheter assembly 2 of FIG. 1, this may increase a difficulty or force necessary to "turn the corner" or move the instrument 42 in a distal direction from the side port 18 through the catheter 14. The force may lead to movement or disruption of the catheter assembly 10. Furthermore, if the angle θ were 45°, this may result in increased bending of the instrument 42, which may be undesirable. Moreover, if the angle θ were 45°, this may result in the instrument 42 contacting a mouth 44 of a wedge 46 as it enters the body fluid path 36, which may cause the instrument 42 to stop or have difficulty progressing distally. In some embodiments, the angle θ may be 45° and other features may be used to facilitate smooth transition of the instrument 42 from the side port fluid path 34 to the body fluid path 36 and through the catheter 14, around a bend. For example, in some embodiments, the angle θ may be 45° and an angle of the mouth 44 may be changed.

In some embodiments, the wedge 46 may be used to secure the catheter 14 within the catheter adapter 12. In some embodiments, the wedge 46 may be funnel-shaped, having the mouth 44 and a stem 48. In some embodiments, the mouth 44 and the stem 48 may be annular. In some embodiments, the mouth may be flared or include a shape of a truncated cone. In some embodiments, the stem 48 may include a constant inner diameter along at least a portion of a length of the stem 48. In some embodiments, the stem 48 may be generally tubular. In some embodiments, the stem 48 may be inserted into the proximal end of the catheter 14. In some embodiments, an inner diameter of the mouth 44 may increase in a proximal direction and may be greater than an inner diameter of the stem 48. In some embodiments, the mouth 44 may press into the catheter adapter 12.

In some embodiments, the angle θ, which may be less than 45°, may direct the instrument 42 directly into the stem 48 as the instrument 42 is advanced distally from the side port 18 through the catheter 14, thus bypassing or preventing contact between the instrument 42 and most or all of the mouth 44. In some embodiments, an inner surface of the mouth 44 may be perpendicular or nearly perpendicular to the central axis 38, and if the instrument 42 contacts the mouth 44, the instrument 42 may stop or have difficulty progressing distally. On the other hand, in some embodiments, the inner surface of the stem 48 may be more parallel to central axis 38, and thus, if the instrument 42 first contacts the stem 48 portion of the wedge 46 as opposed to the mouth 44, the instrument 42 may be redirected down the body fluid path 36 with much less resistance. In some embodiments, a transition radius 50 between the mouth 44 and the stem 48 may be about 0.035". In some embodiments, the transition radius 50 may be between about 0.002" and about 0.015".

Figure 2D:
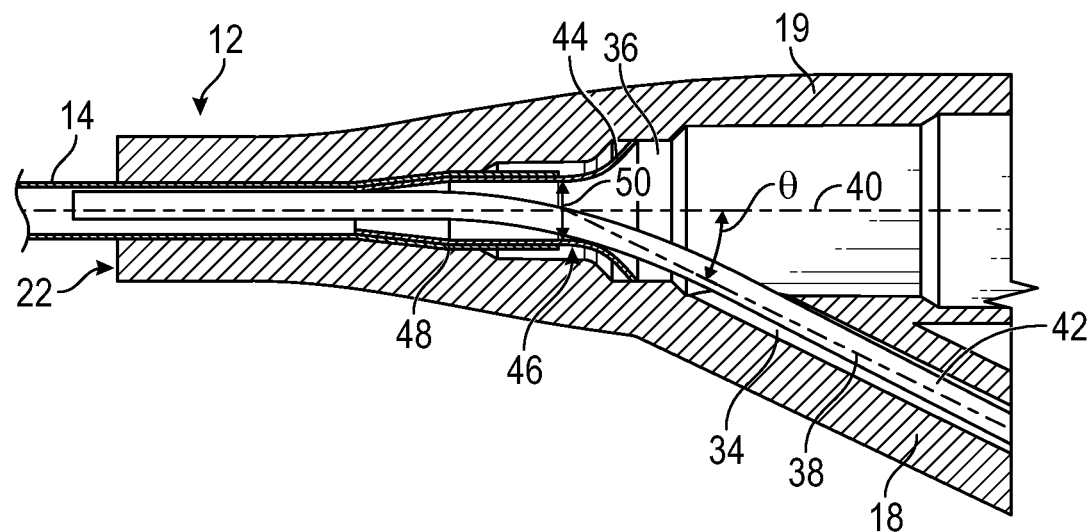
FIG. 2D is a cross-sectional view of another example wedge of the catheter assembly of FIG. 2A, according to some embodiments.

Referring now to FIG. 2D, in some embodiments, the transition radius 50 between the mouth 44 and the stem 48 may be increased from FIG. 2C, for example, which may allow the instrument 42 to curve in a larger radius than before, reducing a force needed advance the instrument 42 around the bend and through the catheter 14. In some embodiments, the wedge 46 may be constructed of metal. In these embodiments, the force may be reduced because the metal may not deform and create a catch point during initial contact with the instrument 42. Metal also tends to have a lower coefficient of friction with other materials than plastic does, which may also reduce the insertion force. In some embodiments, the wedge 46 may be constructed of another suitable material. In some embodiments, an inner surface of the wedge 46 may curved all or a portion of a length of the wedge 46.

In some embodiments, a greater transition radius 50 may be achieved via a smooth transition between the mouth 44 and the stem 48, as illustrated, for example, in FIG. 2D. In some embodiments, the transition radius 50 may be about 0.075". In some embodiments, the transition radius 50 may be between about 0.015" and about 0.100".

Figure 3A:
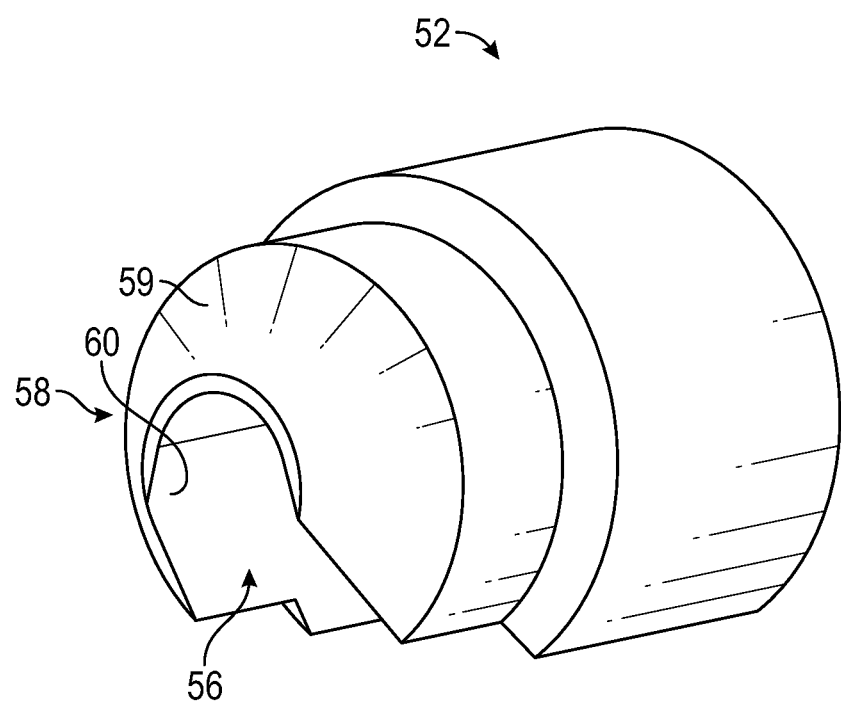
FIG. 3A is an upper perspective view of an example insert of the catheter assembly of FIG. 2A, according to some embodiments.
Figure 3B:
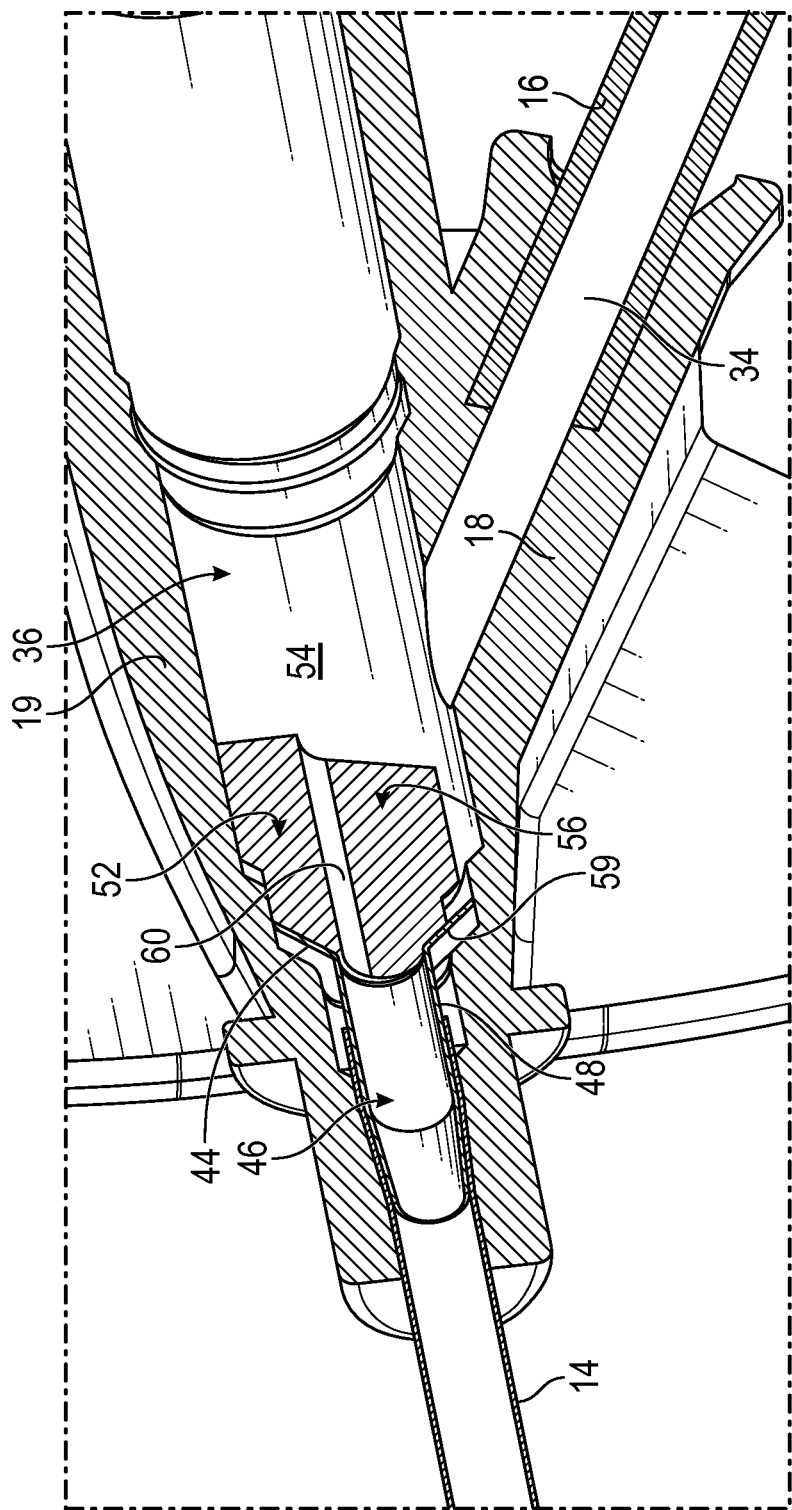
FIG. 3B is a cross-sectional view of the insert of FIG. 3A, according to some embodiments.
Figure 3C:
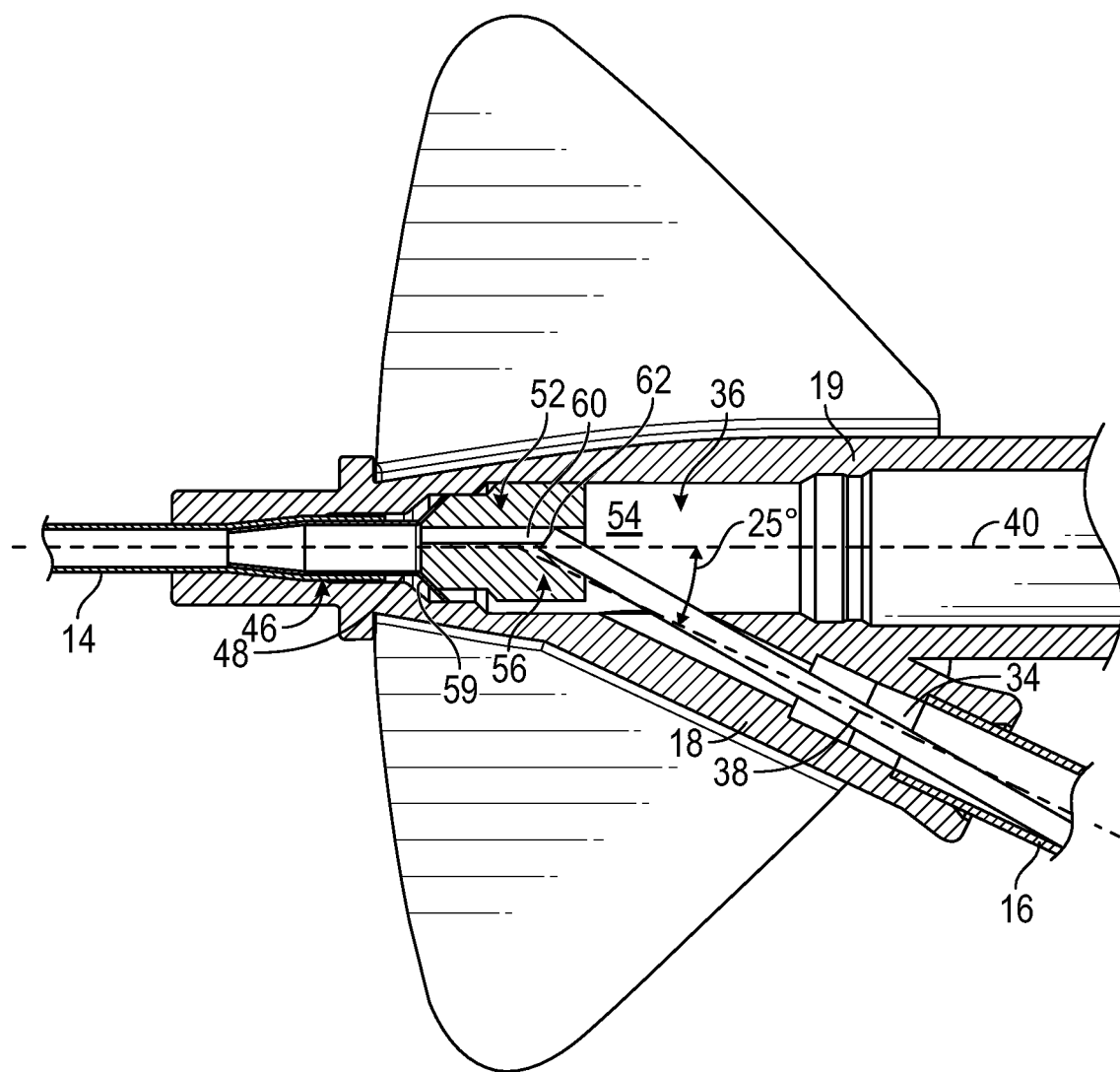
FIG. 3C is another cross-sectional view of the insert of FIG. 3A, illustrating an example instrument, according to some embodiments.

Referring now to FIGS. 3A-3C, in some embodiments, an insert 52 may be disposed within a lumen 54 of the catheter adapter 12, which may include the body fluid path 36. In some embodiments, the insert 52 may facilitate transverse of the bend between the longitudinal axis 40 and the central axis 38 of the side port 18 by the instrument 42. In some embodiments, the insert 52 may be disposed proximate the wedge 46. In some embodiments, the insert 52 may redirect the instrument 42 before it passes a proximal edge of the mouth 44, as illustrated, for example, in FIG. 3C.

In some embodiments, the insert 52 may include a groove 56, which may extend along an entire length of the insert 52. In some embodiments, the insert 52 may be oriented within the lumen 54 such that the groove 56 is aligned with the side port fluid path 34 and fluid may flow from the side port fluid path 34 distally through the insert 52.

In some embodiments, a distal end 58 of the insert 52 may include a tapered portion 59, which may contact the inner surface of the mouth 44. In some embodiments, an angle of the tapered portion 59 may correspond to an angle of the inner surface of the mouth 44 such that the distal end 58 of the insert 52 is fitted within the mouth 44. In some embodiments, an upper portion 60 of the groove 56 may include a generally cylindrical shape and/or may be concentric with a center of the stem 48.

In some embodiments, the generally cylindrical shape of the upper portion 60 may have an inner diameter that is less than the inner diameter of the stem 48 such that the instrument 42 "falls off" the insert 52 into the wedge 46 with no catch point when the instrument 42 is advanced distally. In some embodiments, the insert 52 may extend to the proximal end of the stem 48 such that the generally cylindrical shape of the upper portion 60 leads the instrument 42 directly into the stem 48.

In some embodiments, the instrument 42 may enter the body fluid path 36 from the side port fluid path 34 and a distal end 62 of the instrument 42 may contact the upper portion 60 of the groove 56, without first contacting an inner surface of the body 19 forming the lumen 54. In some embodiments, after contacting the upper portion 60 of the groove 56, the instrument 42 may then slide along the generally cylindrical shape in the distal direction until the instrument 42 enters the stem 48.

In some embodiments, the insert 52 may prevent the instrument 42 from extending far beyond the longitudinal axis 40 of the catheter adapter 12 as the instrument 42 is advanced from the side port 18, which would result in the instrument 42 having to come back to the longitudinal axis 40 to move distally through the stem 48. In these and other embodiments, the distal end 62 of the instrument 42 may be disposed proximate or adjacent the longitudinal axis 40 when the distal end 62 contacts the upper portion 60 of the groove 56.

In some embodiments, the insert 52 may allow the instrument 42 to start bending proximal to the mouth 44 of the wedge 46, which may increase an overall bend radius of the instrument 42 and reduce a force needed to create a bend in the instrument 42. In some embodiments, the insert 52 may be used with the angle θ at 45° or less than 45° (see FIGS. 2C-2D, for example). In some embodiments, the angle θ may be about 25°, which may facilitate distal movement of the instrument 42 through the catheter assembly 10.

In some embodiments, the insert 52 may be asymmetric, which may allow for a much larger bend radius of the instrument 42, thus reducing a peak force required to force the instrument 42 around the bend. In some embodiments, at least a portion of the insert 52 may be transparent. In some embodiments, the wedge 46 may include less of a 360° circle than illustrated in FIG. 3A, which may allow better flashback visibility, or more of a 360° circle. In some embodiments, one or more grooves may be added to an inner surface and/or an outer surface of the insert 52 to improve flushability. In some embodiments, the insert 52 may be constructed of a rigid or semi-rigid material, such as for example, plastic or metal.

Figure 4:
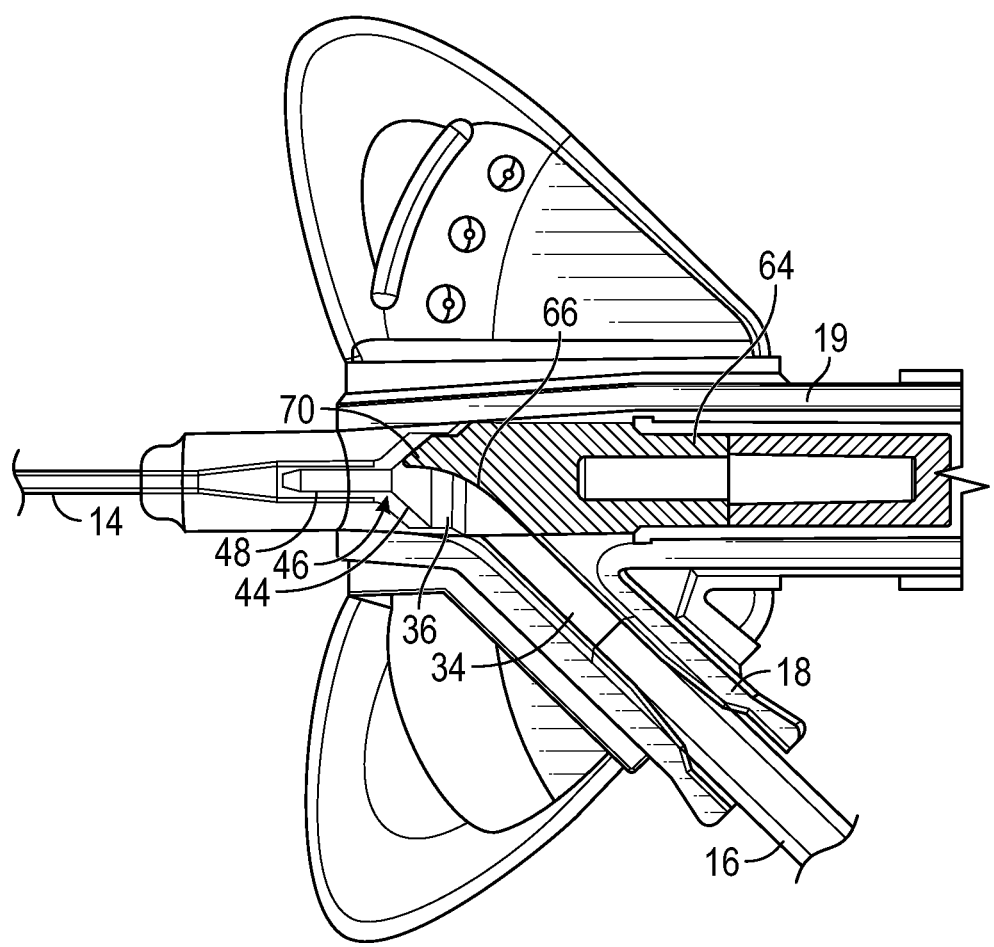
FIG. 4 is a cross-sectional view of an example septum of the catheter assembly of FIG. 2A, according to some embodiments.

Referring now to FIG. 4, in some embodiments, an outer surface of a septum 64 may include a guide portion 66 to direct movement of the instrument 42 as the instrument 42 is advanced distally from the side port 18 through the catheter 14. In some embodiments, at least a portion of the guide portion 66 may include a smooth curve. In some embodiments, the guide portion 66 may be smooth. In some embodiments, the septum 64 may include one or more features of the insert 52. In some embodiments, the septum 64 may be disposed proximate the wedge 46. In some embodiments, the guide portion 66 may redirect the instrument 42 before the instrument 42 passes a proximal edge of the mouth 44, as illustrated, for example, in FIG. 4.

In some embodiments, the septum 64 may be oriented within the lumen 54 such that the guide portion 66 is aligned with the side port fluid path 34 and fluid may flow from the side port fluid path 34 distally along the guide portion 66.

In some embodiments, a distal end of the septum 64 may include a tapered portion 70, which may contact the inner surface of the mouth 44. In some embodiments, an angle of the tapered portion 70 may correspond to an angle of the inner surface of the mouth 44 such that the distal end of the septum 64 is fitted within the mouth 44.

In some embodiments, the distal end of the septum 64 may be positioned closer to the longitudinal axis 40 than the inner surface of the stem 48 such that when the instrument 42 is advanced distally, the instrument 42 "falls off" the guide portion 66 that is proximate the distal end and into the wedge 46 with no catch point. In some embodiments, the septum 64 may extend to the proximal end of the stem 48 such that the septum 64 leads the instrument 42 directly into the stem 48.

In some embodiments, the instrument 42 may enter the body fluid path 36 from the side port fluid path 34 and the distal end 62 of the instrument 42 (see, for example, FIG. 3C) may contact the guide portion 66, without first contacting the inner surface of the body 19 forming the lumen 54. In some embodiments, after contacting the guide portion 66, the instrument 42 may then slide along the guide portion 66 in the distal direction until the instrument 42 enters the stem 48.

In some embodiments, the guide portion 66 may prevent the instrument 42 from extending far beyond the longitudinal axis 40 of the catheter adapter 12 as the instrument 42 is advanced from the side port 18, which would result in the instrument 42 having to come back to the longitudinal axis 40 to move distally through the stem 48. In these and other embodiments, the distal end 62 of the instrument 42 may be disposed proximate or adjacent the longitudinal axis 40 when the distal end 62 contacts the guide portion 66.

In some embodiments, the guide portion 66 may allow the instrument 42 to start bending proximal to the mouth 44 of the wedge 46, which may increase an overall bend radius of the instrument 42 and reduce the force needed to create the bend in the instrument 42. In some embodiments, the guide portion 66 may be used with the angle θ at 45° or less than 45° (see FIGS. 2C-2D, for example). In some embodiments, the angle θ may be about 25°, which may facilitate distal movement of the instrument 42 through the catheter assembly 10.

In some embodiments, the septum 64 may be constructed of a resilient material, such as, for example, silicon rubber or polyisoprene. In some embodiments, the septum 64 may be constructed of another type of material. In some embodiments, the septum 64 may include one, two, three or more pieces.

Figure 5A:
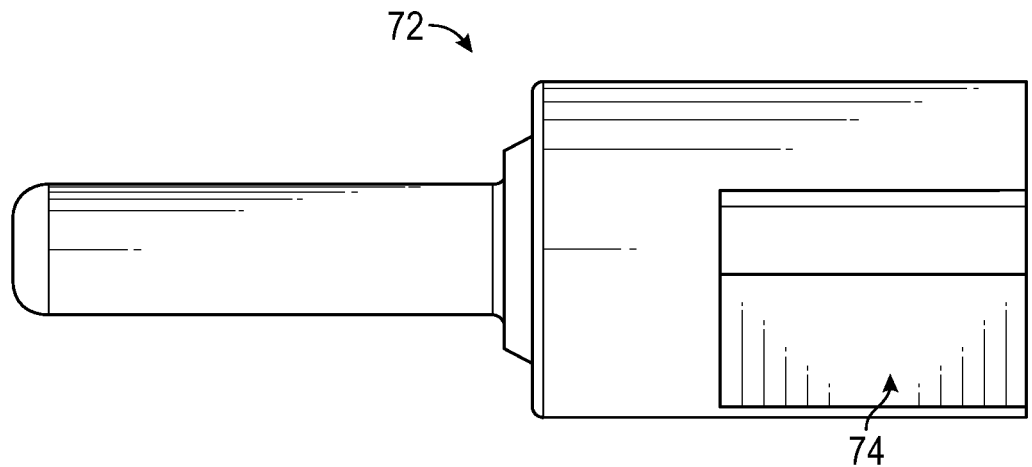
FIG. 5A is an upper perspective view of another example wedge, according to some embodiments.
Figure 5B:
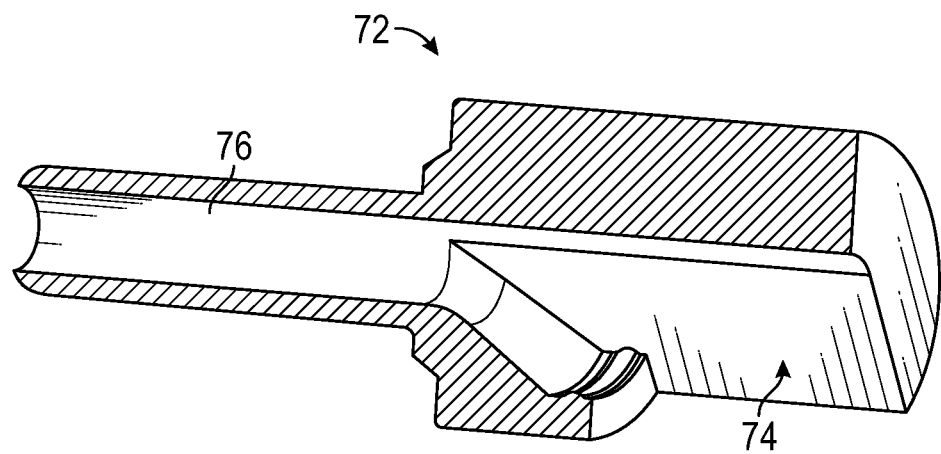
FIG. 5B is a cross-sectional view of the wedge of FIG. 5A, according to some embodiments.
Figure 5C:
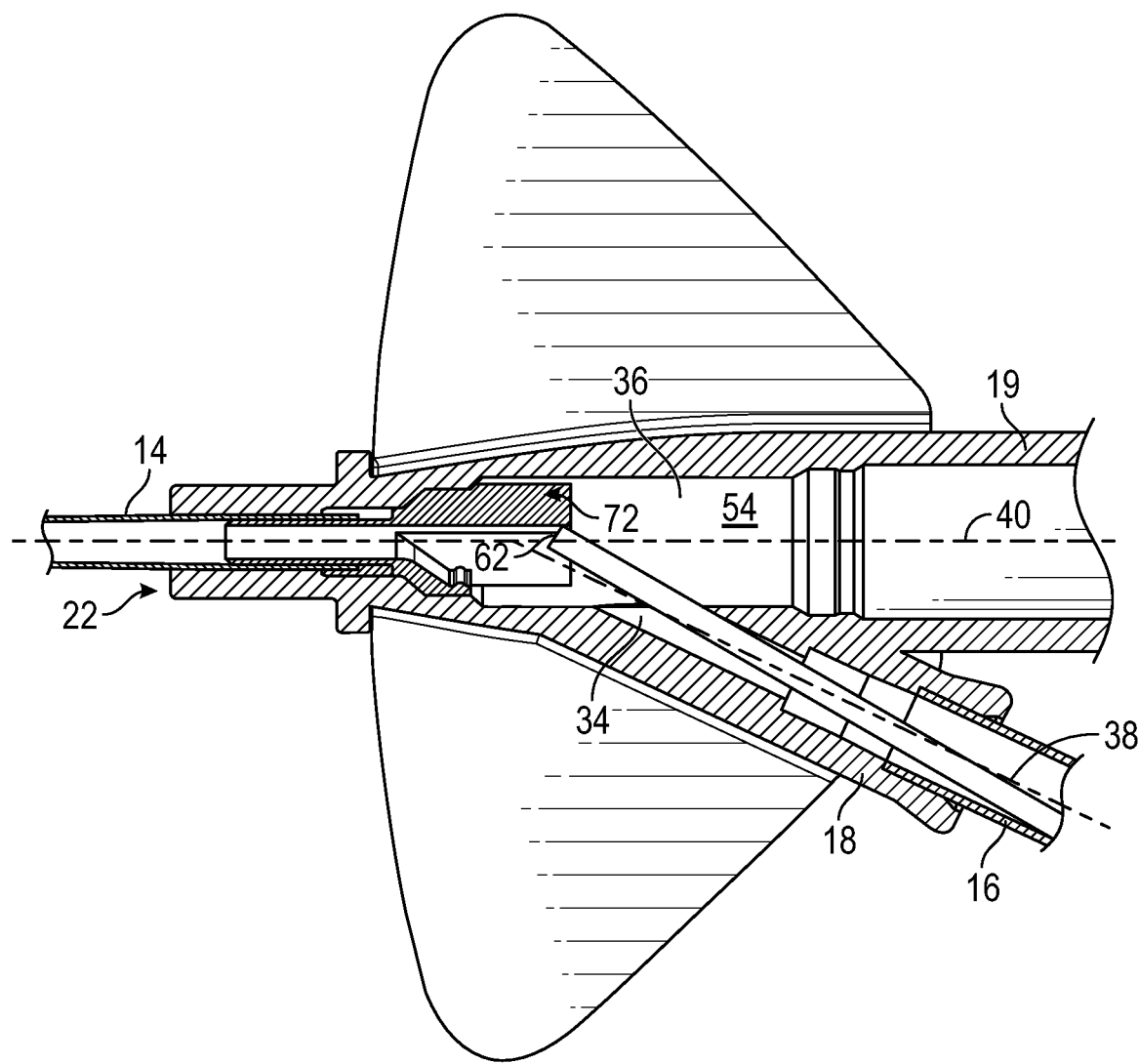
FIG. 5C is a cross-sectional view of the wedge of FIG. 5A disposed within the catheter assembly of FIG. 2A, according to some embodiments.

Referring now to FIGS. 5A-5C, a wedge 72 is illustrated, according to some embodiments. In some embodiments, the wedge 72 may include one or more features of the insert 52 described with respect to FIGS. 3A-3C. In some embodiments, the wedge 72 may facilitate transverse of the bend between the longitudinal axis 40 and the central axis 38 of the side port 18 by the instrument 42. In some embodiments, the wedge 72 may connect the catheter 14 to the catheter adapter 12.

In some embodiments, the wedge 72 may include a groove 74, which may extend along a proximal end of the wedge 72. In some embodiments, the wedge 72 may be oriented within the lumen 54 such that the groove 74 is aligned with the side port fluid path 34 and fluid may flow from the side port fluid path 34 distally through the groove 74 and into a tunnel 76 of the wedge 72. In some embodiments, the tunnel 76 may be generally cylindrical.

In some embodiments, the instrument 42 may enter the body fluid path 36 from the side port fluid path 34 and a distal end 62 of the instrument 42 may contact the groove 74, as illustrated, for example in FIG. 5C. In some embodiments, after contacting the groove 74, the instrument 42 may then slide along the groove 74 in the distal direction until the instrument 42 enters and/or proceeds through the tunnel 76. In some embodiments, the wedge 72 may prevent the instrument 42 from extending far beyond the longitudinal axis 40 of the catheter adapter 12 as the instrument 42 is advanced from the side port 18.

In some embodiments, the wedge 72 may be used with the angle θ at 45° or less than 45° (see FIGS. 2C-2D, for example). In some embodiments, the angle θ may be about 25°, which may facilitate distal movement of the instrument 42 through the catheter assembly 10. In some embodiments, the wedge 72 may be asymmetric, which may allow for a much larger bend radius of the instrument 42, thus reducing a peak force required to force the instrument 42 around the bend.

In some embodiments, at least a portion of the wedge 72 may be transparent. In some embodiments, the groove 74 may include less of a 360° circle than illustrated in FIG. 5A to allow for better flashback visibility or more of a 360° circle. In some embodiments, one or more grooves may be added to an inner surface and/or an outer surface of the wedge 72 to improve flushability. In some embodiments, the wedge 72 may be constructed of a rigid or semi-rigid material, such as for example, plastic or metal.

Figure 6:
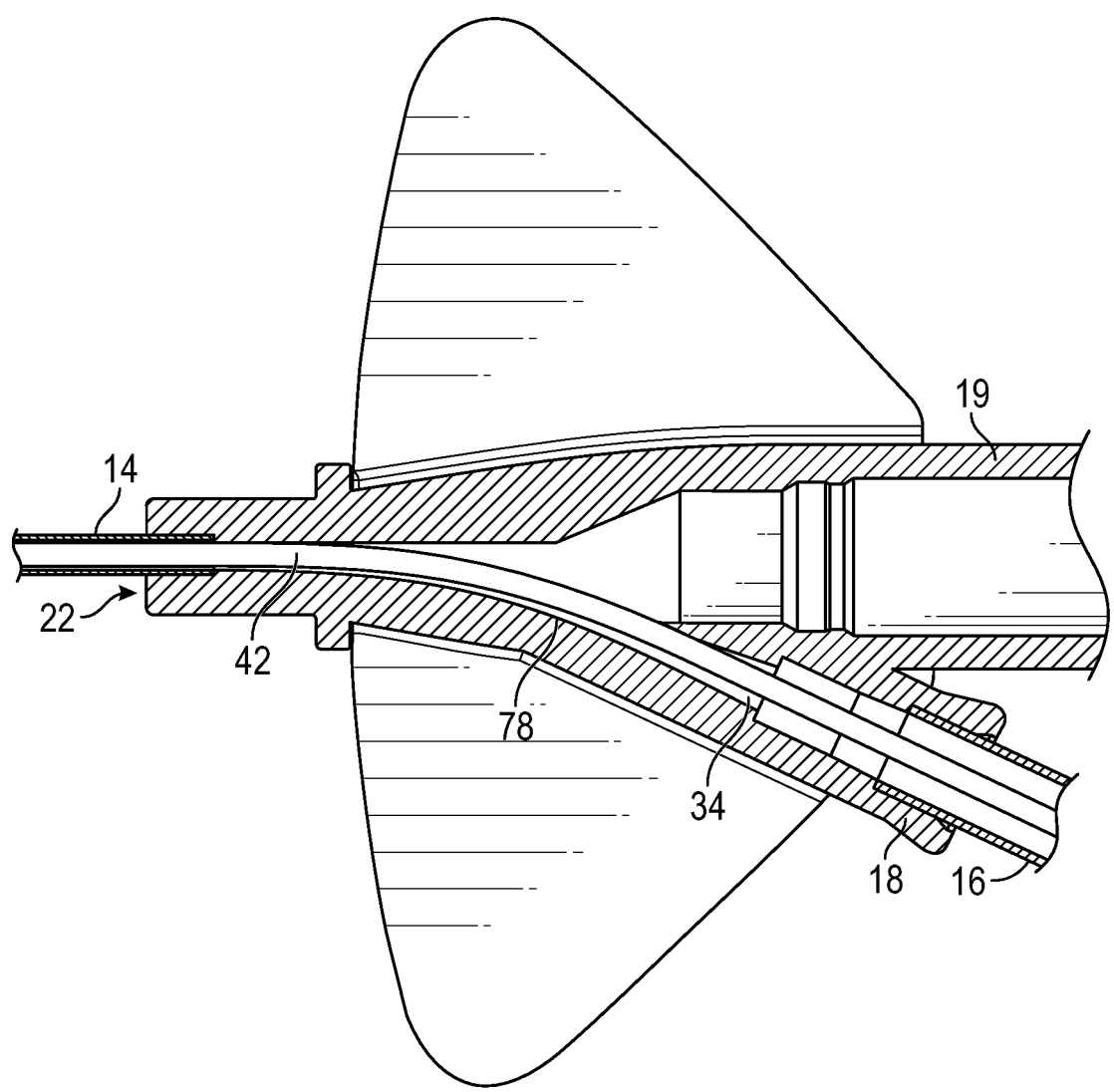
FIG. 6 is a cross-sectional view of the catheter assembly of FIG. 2A, illustrating an example catheter glued within an example catheter adapter, according to some embodiments.

Referring now to FIG. 6, in some embodiments, the catheter adapter 12 may not include a wedge. Instead, in some embodiments, a proximal end of the catheter 14 may be glued within the distal end 22 of the catheter adapter 12. In some embodiments, without the wedge, a diameter of the body fluid path 36 may increase to facilitate an increased bend radius of the instrument 42. In some embodiments, a portion of the inner surface of the body 19 of the catheter adapter 12 proximate a bend in the instrument 42 may be removed to facilitate the increased bend radius. In some embodiments, the inner surface of the body 19 may be asymmetric.

In some embodiments, the inner surface of the body 19 may include a curve 78, which may be smooth. In some embodiments, the curve 78 may extend to the side port fluid path 34 and may be flush with an inner surface of the side port 18 such that there is no catch point at a transition between the side port 18 and the body 19. In some embodiments, the angle θ may be 45° or less than 45° (see FIGS. 2C-2D, for example). In some embodiments, the angle θ may be about 25°, which may facilitate distal movement of the instrument 42 through the catheter assembly 10.

Figure 7:
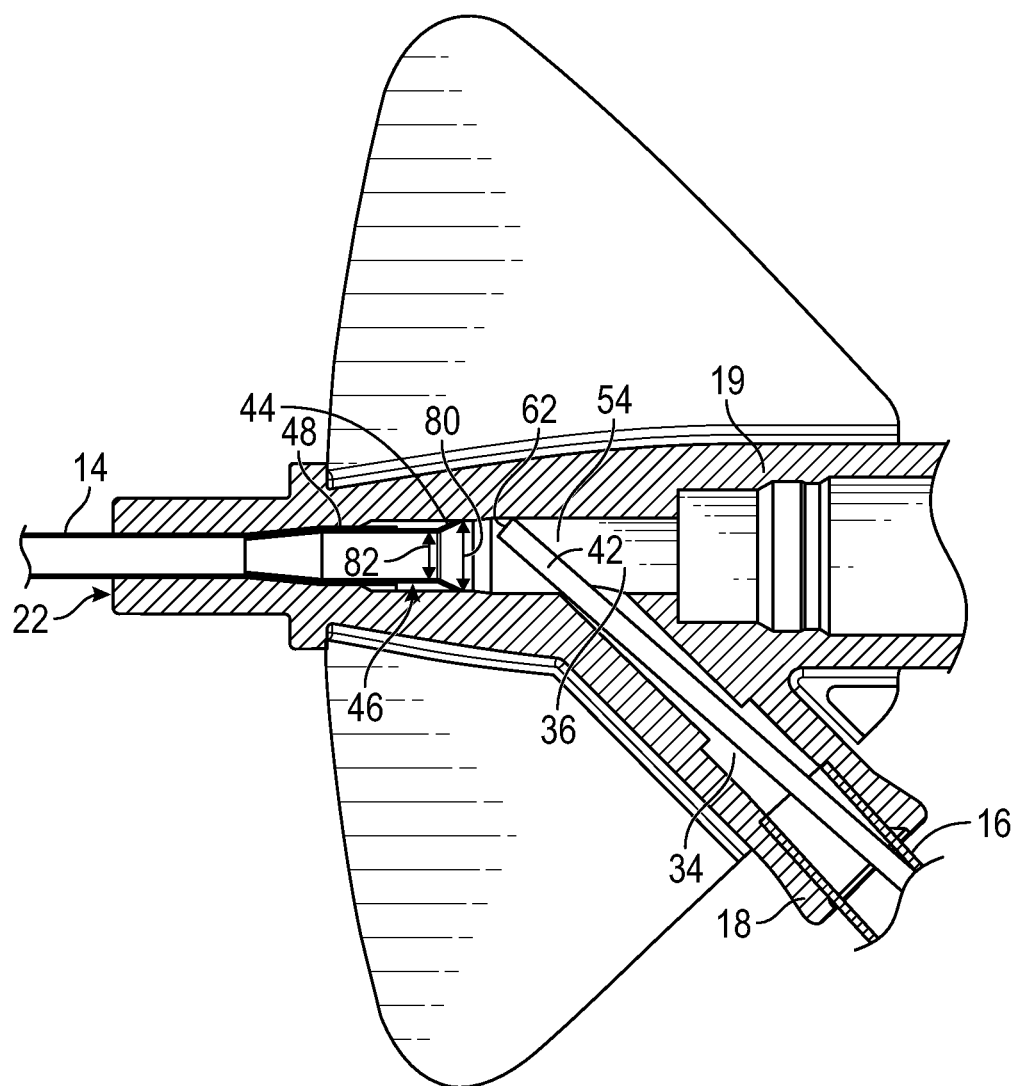
FIG. 7 is a cross-sectional view of another example wedge secured within the catheter assembly of FIG. 2A, according to some embodiments.

Referring now to FIG. 7, in some embodiments, a diameter 80 of the mouth 44 of the wedge 46 may be reduced to slightly larger than a diameter 82 of the stem 48. In some embodiments, the diameter 80 may be disposed at a proximal end of the mouth 44, as illustrated in FIG. 7. In some embodiments, the diameter 80 may be just large enough to allow for placement of a wall of the catheter 14 between the wedge 46 and the inner surface of the body 19 and a press interface between the mouth 44 and the inner surface of the body 19. In some embodiments, the diameter 80 may be between about 0.005" and about 0.020".

In some embodiments, the diameter 80 of the mouth 44 may limit a distance the distal end 62 of the instrument 42 extends across the longitudinal axis 40 as the instrument 42 is advanced distally. In some embodiments, features illustrated in one or more of the Figures of the present disclosure may be combined. For example, the diameter 80 of the mouth 44 may be used in combination with the curve 78, described with respect to FIG. 6.

Figure 8:
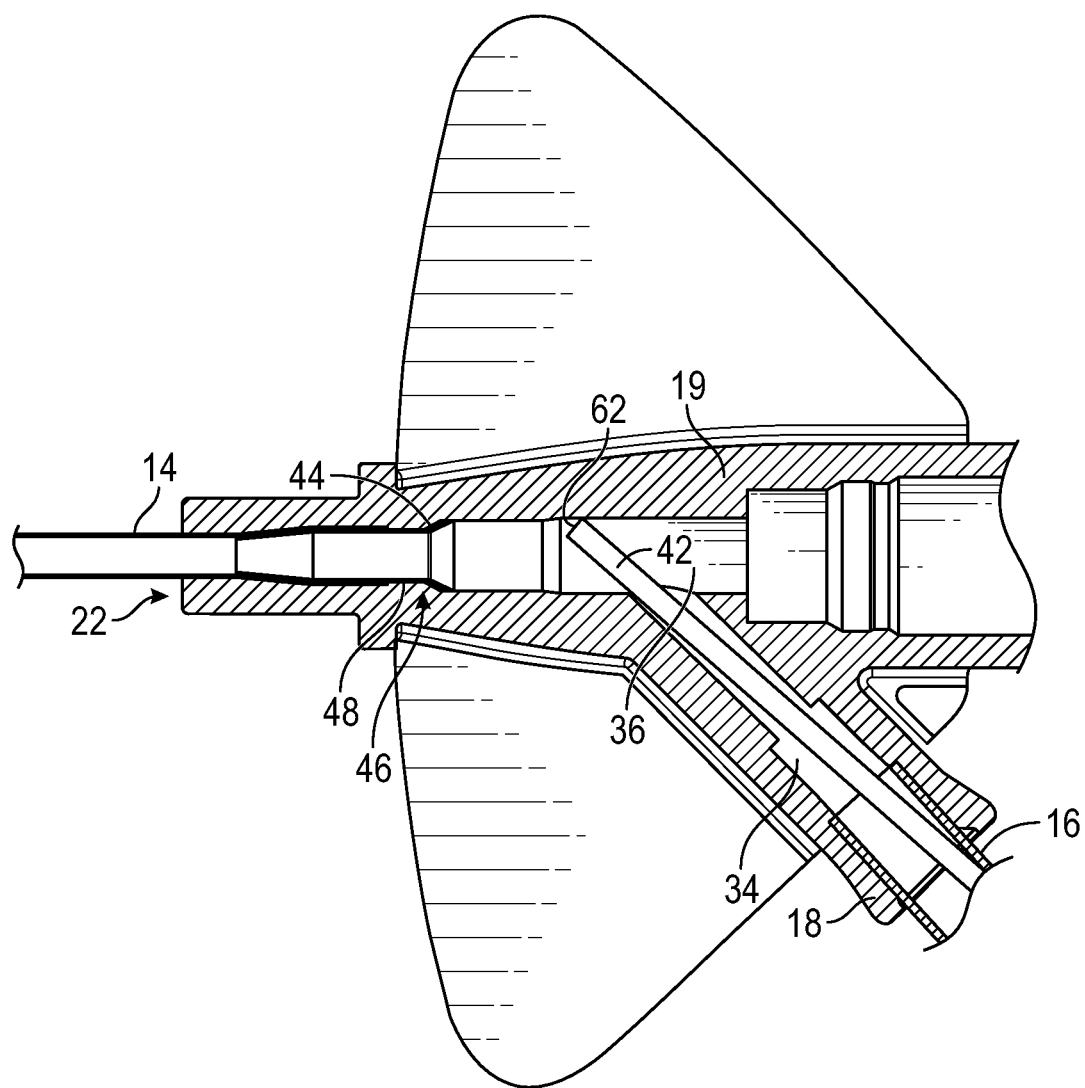
FIG. 8 is a cross-sectional view of another example wedge secured within a distal end of the catheter assembly of FIG. 2A, according to some embodiments.

Referring now to FIG. 8, in some embodiments, the wedge 46 may be disposed within the distal end 22 of the catheter adapter 12 and spaced apart from the side port fluid path 34. In some embodiments, the instrument 42 may enter the body fluid path 36 from the side port fluid path 34 and a distal end 62 of the instrument 42 may contact the inner surface of the body 19, as illustrated in FIG. 8, without first contacting the mouth 44 of the wedge 46. In some embodiments, the inner surface of the body 19 may be smooth and may facilitate sliding of the distal end 62 of the instrument 42 is a distal direction without stopping or having difficulty progressing distally.

Figure 9:
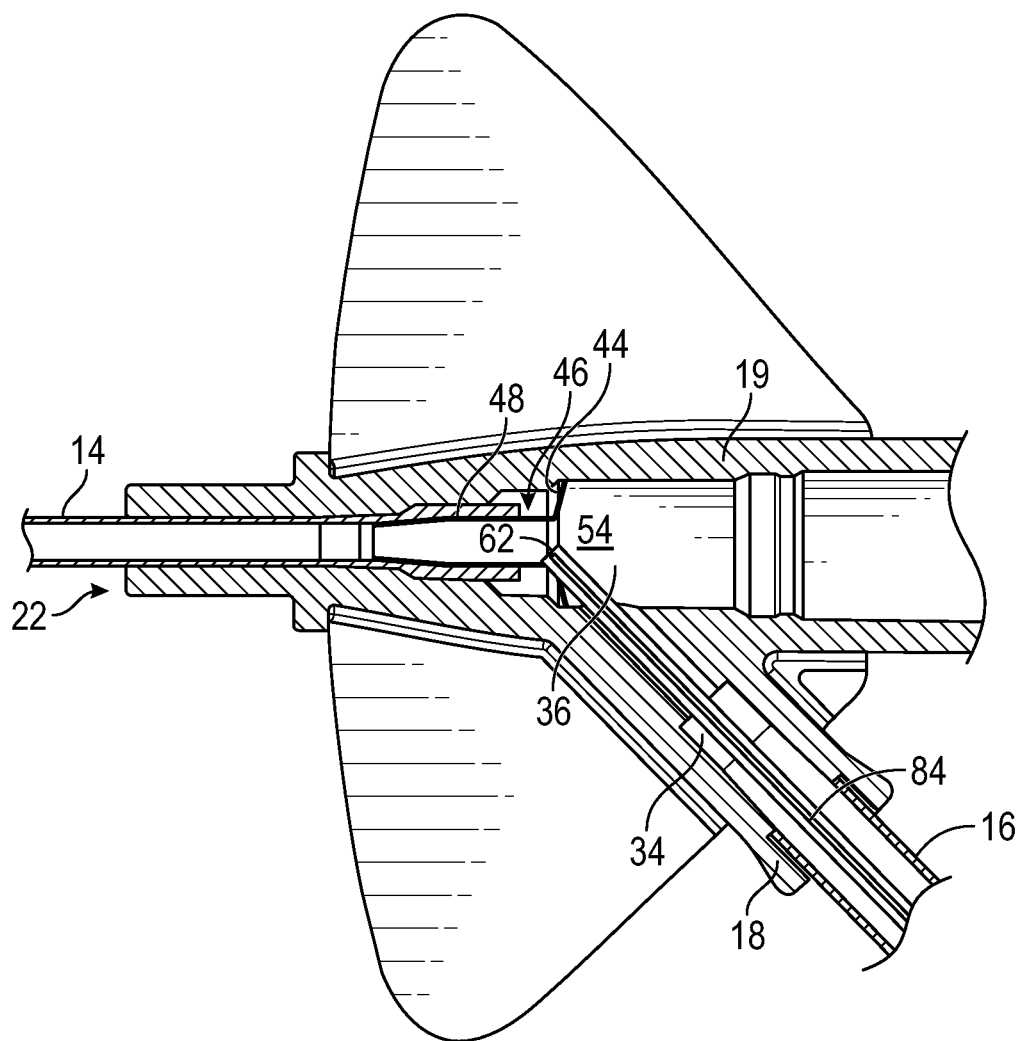
FIG. 9 is a cross-sectional view of another example wedge secured within the catheter assembly of FIG. 2A, according to some embodiments.

Referring now to FIG. 9, in some embodiments, the mouth 44 of the wedge 46 may be shallow and/or the mouth 44 may be disposed proximate or adjacent the side port fluid path 34. In these and other embodiments, the instrument 42 may enter the body fluid path 36 from the side port fluid path 34 and a distal end 62 of the instrument 42 may contact a side of the mouth 44 closer to the side port 18 without first contacting the inner surface of the body 19. In some embodiments, the instrument 42 may then slide distally across the wedge 46 until the instrument 42 enters the stem 48.

In some embodiments, the inner surface of the mouth 44 may be angled between 60° and 90° with respect to the longitudinal axis 40. In some embodiments, a largest outer diameter of the wedge 46 may be approximately equal to an inner diameter of the body 19 proximate or adjacent the side port fluid path 34.

In some embodiments, a guidewire 84 may be disposed within the instrument 42, which may facilitate advancement of the instrument 42 from the side port 18 around the bend to generally align with the longitudinal axis 40.

Figure 10:
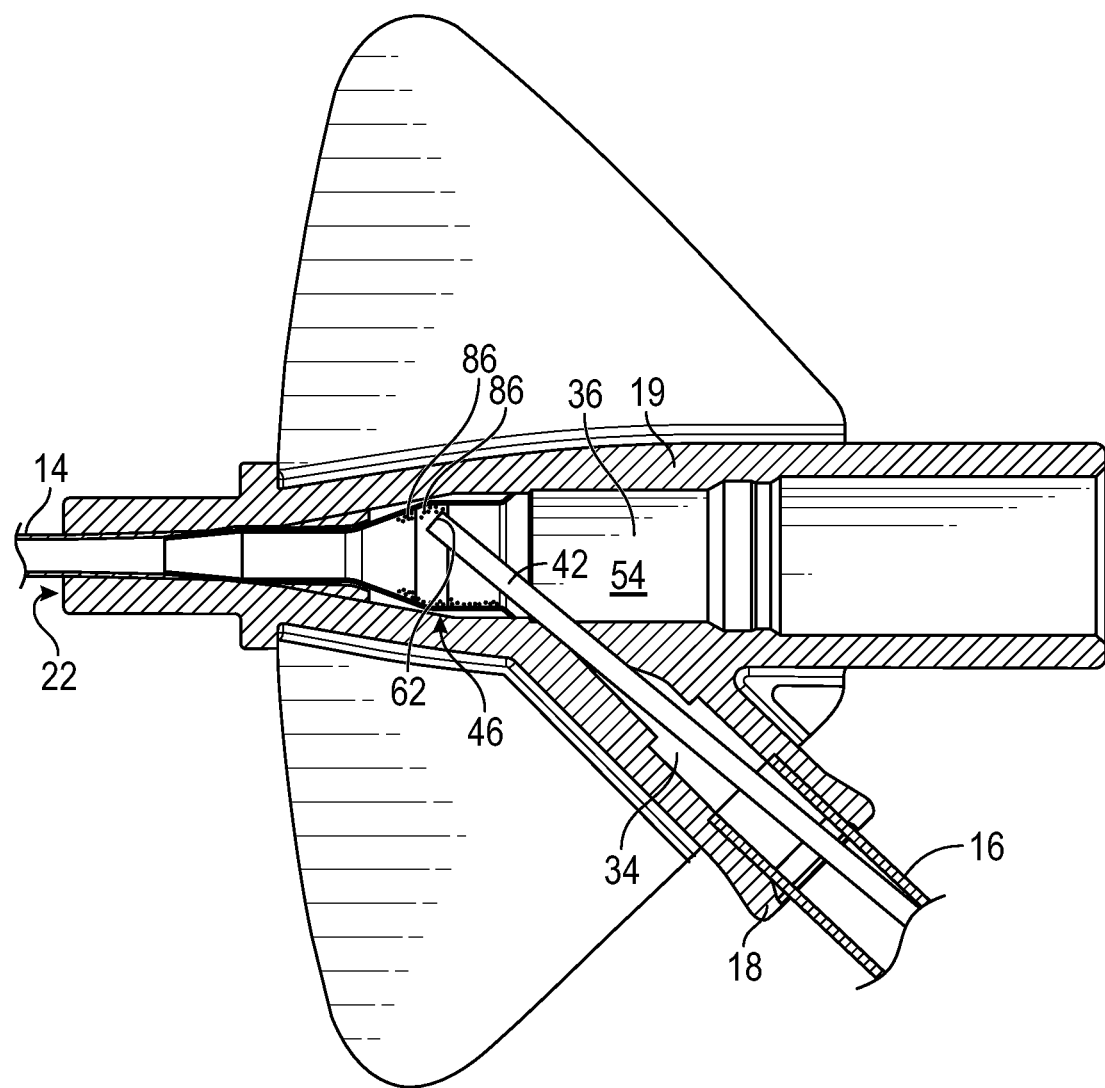
FIG. 10 is a cross-sectional view of another example wedge secured within the catheter assembly of FIG. 2A, according to some embodiments.

Referring now to FIG. 10, in some embodiments, a proximal portion of the wedge 46 may include an increased diameter with a gradual and smooth slope, which may guide the instrument as the instrument is advanced distally from the side port 18. In some embodiments, the gradual and smooth slope may facilitate bending of the instrument 42 and alignment of the instrument 42 with the longitudinal axis 40 with little friction. In some embodiments, the increased diameter may facilitate a larger bend radius of the instrument, which may reduce a force needed advance the instrument 42 around the bend and through the catheter 14.

In some embodiments, all or a portion of an inner surface of one or more of the following may include a lubricious material 86: the wedge 46, the wedge 72, the septum 64, and the insert 52. In some embodiments, the lubricious material 86 may reduce friction and facilitate movement of the instrument 42 in the distal direction.

Figure 11:
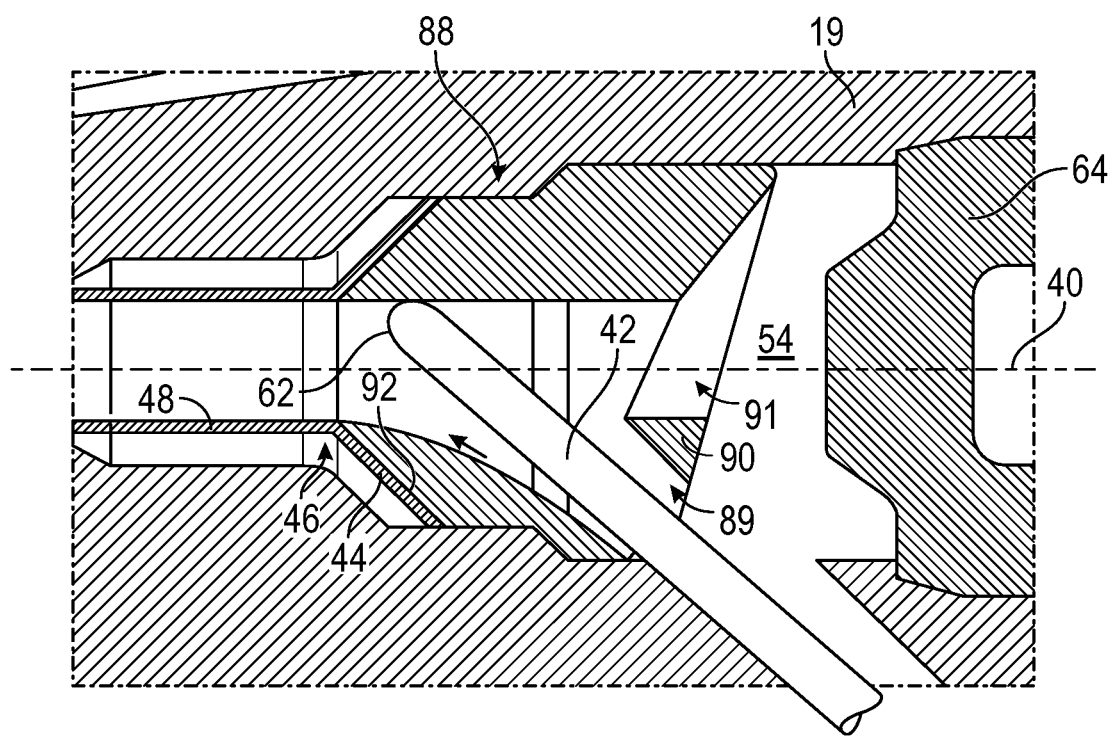
FIG. 11 is a cross-sectional view of another example insert secured within the catheter assembly of FIG. 2A, according to some embodiments.

Referring now to FIG. 11, another insert 88 is illustrated, according to some embodiments. In some embodiments, the insert 88 may include or correspond to the insert 52 of FIGS. 3A-3C. In further detail, in some embodiments, the insert 88 may include one or more features of the insert 52. In some embodiments, the insert 52 may include one or more features of the insert 88.

In some embodiments, the insert 88 may be disposed within the lumen 54 of the catheter adapter 12 and may facilitate transverse of the bend between the longitudinal axis 40 and the central axis 38 of the side port 18 by the instrument 42. In some embodiments, the insert 88 may be disposed proximate the wedge 46. In some embodiments, the insert 88 may redirect the instrument 42 before it passes a proximal edge of the mouth 44, as illustrated, for example, in FIG. 11.

In some embodiments, the insert 88 may be oriented within the lumen 54 such that an opening 89 is aligned with the side port fluid path 34. In some embodiments, fluid flowing into the body 19 of the catheter adapter 12 from the side port fluid path 34 may flow through the opening 89. In some embodiments, after the fluid flows through the opening 89, the fluid may flow distally through the insert 88 and proximally through the insert 88. In further detail, in some embodiments, the insert 88 may include a flushing feature 90, which may be disposed proximate and proximal to the opening 89. In some embodiments, the flushing feature 90 may direct a portion of the fluid flowing into the body 19 proximally through another opening 91 and into a portion of the lumen 54 between the insert 88 and a distal face of the septum 64. Thus, in some embodiments, the flushing feature 90 may facilitate flushing of the portion of the lumen 54 between the insert 88 and the distal face of the septum 64. In some embodiments, the flushing feature 90 may be triangular and may split the fluid flowing into the body 19 from the side port fluid path 34 to force some of the fluid proximally and some distally. In some embodiments, the instrument 42 may extend through the opening 89.

In some embodiments, a distal end 58 of the insert 88 may include a tapered portion 92, which may contact the inner surface of the mouth 44. In some embodiments, an angle of the tapered portion 92 may correspond to an angle of the inner surface of the mouth 44 such that the distal end 58 of the insert 88 fits snugly within the mouth 44.

In some embodiments, an inner surface of the insert 88 proximate the stem 48 may have a diameter less than the inner diameter of the stem 48 such that the instrument 42 "falls off" the insert 88 into the wedge 46 with no catch point when the instrument 42 is advanced distally. In some embodiments, the diameter of the inner surface of the insert 88 proximate the stem 48 may be equal to the inner diameter of the stem 48. In some embodiments, the insert 88 may extend to the proximal end of the stem 48 such that the insert 88 leads the instrument 42 directly into the stem 48.

In some embodiments, the instrument 42 may enter the body fluid path 36 from the side port fluid path 34 and a distal end 62 of the instrument 42 may contact the inner surface of the insert 88, without first contacting the inner surface of the body 19 forming the lumen 54. In some embodiments, after contacting the inner surface of the insert 88, the instrument 42 may then slide along the inner surface of the insert 88 in the distal direction until the instrument 42 enters the stem 48.

In some embodiments, the insert 88 may prevent the instrument 42 from extending far beyond the longitudinal axis 40 of the catheter adapter 12 as the instrument 42 is advanced from the side port 18, which would result in the instrument 42 having to come back to the longitudinal axis 40 to move distally through the stem 48. In these and other embodiments, the distal end 62 of the instrument 42 may be disposed proximate or adjacent the longitudinal axis 40 when the distal end 62 contacts the inner surface of the insert 88.

In some embodiments, the insert 88 may allow the instrument 42 to start bending proximal to the mouth 44 of the wedge 46, which may increase an overall bend radius of the instrument 42 and reduce a force needed to create a bend in the instrument 42. In some embodiments, the insert 88 may be asymmetric, which may allow for a much larger bend radius of the instrument 42, thus reducing a peak force required to force the instrument 42 around the bend.

In some embodiments, at least a portion of the insert 88 may be transparent. In some embodiments, one or more grooves may be added to an inner surface and/or an outer surface of the insert 88 to improve flushability. In some embodiments, the insert 88 may be constructed of a rigid or semi-rigid material, such as for example, plastic or metal.

Figure 12:
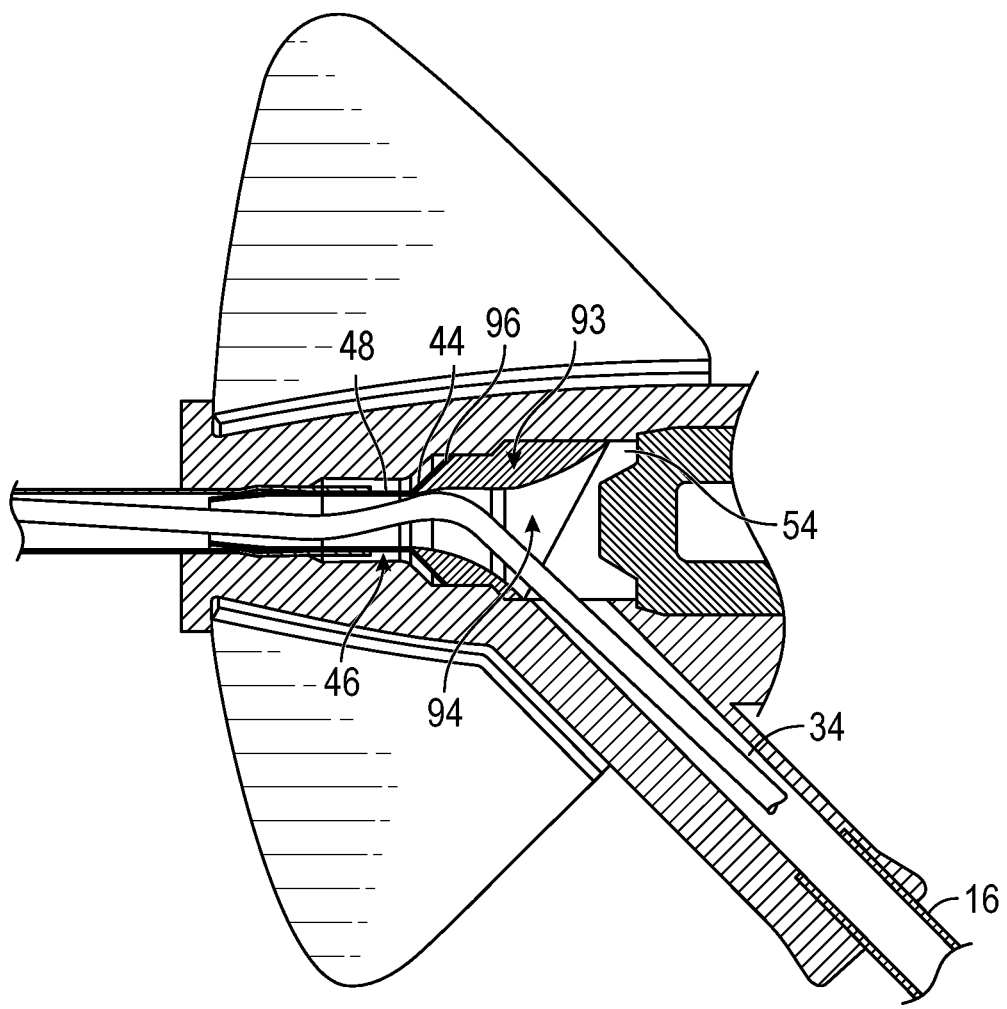
FIG. 12 is a cross-sectional view of another example insert secured within the catheter assembly of FIG. 2A, according to some embodiments.

Referring now to FIG. 12, another insert 93 is illustrated, according to some embodiments. In some embodiments, the insert 93 may include or correspond to the insert 52 of FIGS. 3A-3C and/or the insert 88 of FIG. 11. In further detail, in some embodiments, the insert 93 may include one or more features of the insert 52 and/or the insert 88.

In some embodiments, the insert 93 may be disposed within the lumen 54 of the catheter adapter 12 and may facilitate transverse of the bend between the longitudinal axis 40 and the central axis 38 of the side port 18 by the instrument 42. In some embodiments, the insert 93 may be disposed proximate the wedge 46. In some embodiments, the insert 93 may redirect the instrument 42 before it passes a proximal edge of the mouth 44.

In some embodiments, the insert 93 may be oriented within the lumen 54 such that an opening 94 is aligned with the side port fluid path 34 and fluid may flow from the side port fluid path 34 distally through the insert 93. In some embodiments, a distal end 58 of the insert 93 may include a tapered portion 96, which may contact the inner surface of the mouth 44. In some embodiments, an angle of the tapered portion 96 may correspond to an angle of the inner surface of the mouth 44 such that the distal end 58 of the insert 93 fits snugly within the mouth 44.

In some embodiments, an inner surface of the insert 93 proximate the stem 48 may have a diameter less than the inner diameter of the stem 48 such that the instrument 42 "falls off" the insert 93 into the wedge 46 with no catch point when the instrument 42 is advanced distally. In some embodiments, the diameter of the inner surface of the insert 93 proximate the stem 48 may be equal to the inner diameter of the stem 48. In some embodiments, the insert 93 may extend to the proximal end of the stem 48 such that the insert 93 leads the instrument 42 directly into the stem 48.

In some embodiments, the instrument 42 may enter the body fluid path 36 from the side port fluid path 34 and a distal end 62 of the instrument 42 may contact the inner surface of the insert 93, without first contacting the inner surface of the body 19 forming the lumen 54. In some embodiments, after contacting the inner surface of the insert 93, the instrument 42 may then slide along the inner surface of the insert 93 in the distal direction until the instrument 42 enters the stem 48.

In some embodiments, the insert 93 may prevent the instrument 42 from extending far beyond the longitudinal axis 40 of the catheter adapter 12 as the instrument 42 is advanced from the side port 18, which would result in the instrument 42 having to come back to the longitudinal axis 40 to move distally through the stem 48. In these and other embodiments, the distal end 62 of the instrument 42 may be disposed proximate or adjacent the longitudinal axis 40 when the distal end 62 contacts the inner surface of the insert 93.

In some embodiments, the insert 93 may allow the instrument 42 to start bending proximal to the mouth 44 of the wedge 46, which may increase an overall bend radius of the instrument 42 and reduce a force needed to create a bend in the instrument 42. In some embodiments, the insert 93 may be asymmetric, which may allow for a much larger bend radius of the instrument 42, thus reducing a peak force required to force the instrument 42 around the bend.

In some embodiments, at least a portion of the insert 93 may be transparent. In some embodiments, one or more grooves may be added to an inner surface and/or an outer surface of the insert 93 to improve flushability. In some embodiments, the insert 93 may be constructed of a rigid or semi-rigid material, such as for example, plastic or metal.

Figure 13:
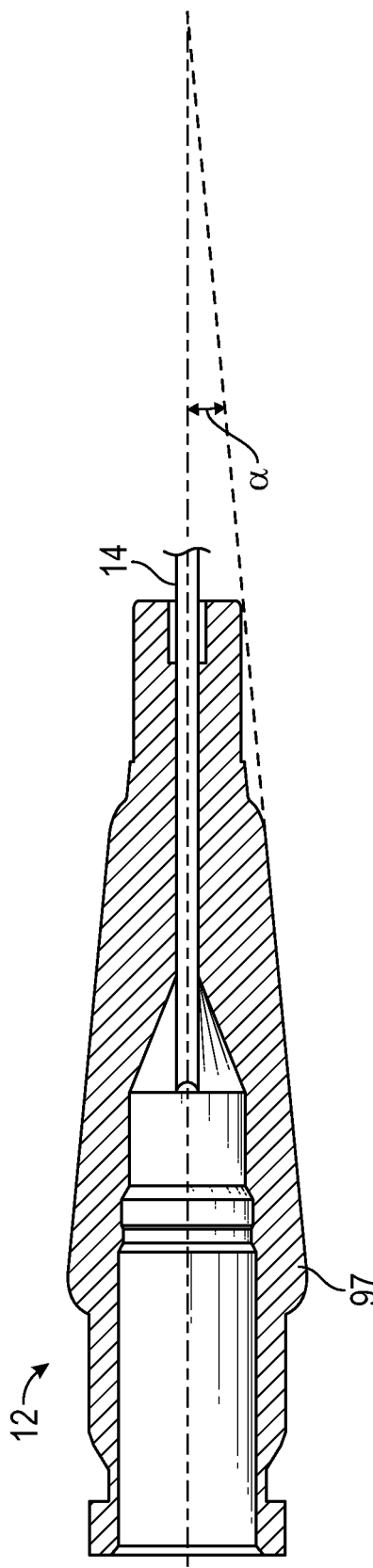
FIG. 13 is a cross-sectional view of an example platform of an example catheter adapter of the catheter assembly of FIG. 2A, according to some embodiments.

Referring now to FIG. 13, in some embodiments, a bottom of the catheter adapter 12 may include a protruding platform 97, which may raise the catheter adapter 12 and the catheter 14 with respect to the skin of the patient. In some embodiments, the platform 97 may facilitate positioning the catheter adapter 12 and the catheter 14 at an angle of about 30° with respect to the skin, which may be about equal to an insertion angle of the catheter 14 into the skin. Thus, in some embodiments, the platform 97 may reduce an "S shape" which may result from inserting the catheter 14 into the skin at an angle and then letting the catheter adapter 12 sit flat on the skin. In some embodiments, an angle α of the platform 97 with respect to the longitudinal axis 40 of the catheter adapter 12 may be about 6°. In some embodiments, the angle α of the platform 97 with respect to the longitudinal axis 40 of the catheter adapter 12 may be between about 3° and 8°. In some embodiments, the angle α of the platform 97 with respect to the longitudinal axis 40 of the catheter adapter 12 may be between about 3° and about 30°. In some embodiments, a top of the catheter adapter 12 may or may not include a platform similar to platform 97. In some embodiments, the platform 97 may be planar.

Figure 14:
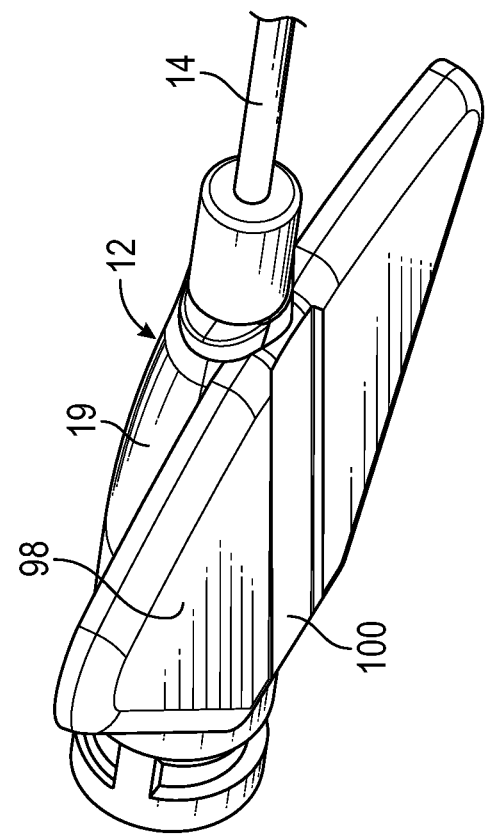
FIG. 14 is a lower perspective view of an example catheter adapter of the catheter assembly of FIG. 2A, according to some embodiments.

Referring now to FIG. 14, in some embodiments, the catheter adapter 12 may be coupled to a securement platform 98, which may include one or more wings. In some embodiments, include a bottom surface of the securement platform 98 may be configured to contact the skin of the patient. In some embodiments, the bottom surface of the securement platform 98 may be generally planar or flat and may include a groove 100 extending along the longitudinal axis of the catheter adapter 12. In some embodiments, the groove 100 may act as a relief feature to relieve pressure on the vasculature of the patient and prevent vein occlusion. Typically a portion of a particular catheter assembly that contacts the skin may be rounded or include another geometry that creates a pressure point on the vasculature.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present inventions have been described in detail, it should be understood that the various changes, substitutions, and alterations could be made hereto without departing from the spirit and scope of the invention.

The invention claimed is:

1. A catheter assembly, comprising:
   a catheter adapter having a distal end, a proximal end, a lumen extending between the distal end and the proximal end, and a side port, wherein a central axis of a fluid path extending through the side port is disposed at an angle with respect to a longitudinal axis of the catheter adapter;
   a septum disposed within the lumen of the catheter adapter;
   a wedge disposed within the lumen of the catheter adapter and distal to the septum; and
   an insert proximate the wedge, wherein the insert is configured to guide an instrument moving from the side port distally through the catheter adapter.

2. The catheter assembly of claim 1, wherein the angle is about 25°.

3. The catheter assembly of claim 1, wherein the insert is constructed of a rigid or semi-rigid material.

4. The catheter assembly of claim 1, wherein the wedge is constructed of metal.

5. The catheter assembly of claim 1, wherein an inner surface of the wedge or the insert comprises a lubricant.

6. The catheter assembly of claim 1, wherein the insert comprises a groove extending along an entire length of the insert and forming a side opening in the insert, wherein the groove is aligned with the side port fluid path such that fluid may flow from the side port fluid path distally through the insert.

7. The catheter assembly of claim 6, wherein the wedge comprises a mouth that includes a shape of a truncated cone, wherein a distal end of the insert comprises a tapered portion that contacts an inner surface of the mouth.

8. The catheter assembly of claim 7, wherein the wedge further comprises a stem proximate the mouth, wherein a portion of the groove is disposed proximate the stem and aligned with a central axis of the stem, wherein an inner diameter of the portion of the groove is less than or equal to an inner diameter of the stem.

9. The catheter assembly of claim 1, further comprising a catheter extending distally from the catheter adapter, wherein a proximal end of the catheter is glued within a distal end of the catheter adapter.

10. The catheter assembly of claim 1, wherein the wedge comprises a mouth that includes a shape of a truncated cone, wherein the wedge further comprises a stem proximate the mouth, wherein the wedge is configured such that the instrument advanced distally from the side port through the catheter adapter contacts an inner surface of the stem without contacting an inner surface of the mouth.

11. The catheter assembly of claim 1, wherein the wedge comprises a mouth that includes a shape of a truncated cone, wherein an inner surface of the mouth is angled between about 60° and about 90° with respect to the longitudinal axis, wherein the instrument advanced distally from the side port through the catheter adapter contacts an inner surface of a first side of the mouth closer to the side port without or prior to a side of the mouth opposite the first side.

12. The catheter assembly of claim 1, wherein the instrument comprises a tube, further comprising a guidewire extending through the tube.

13. The catheter assembly of claim 1, further comprising a platform protruding from a bottom of the catheter adapter and configured to contact skin of a patient, wherein the platform is angled between about 3° and about 30° with respect to the longitudinal axis.

14. The catheter assembly of claim 1, wherein a bottom of the catheter adapter comprises a securement platform configured to contact skin of a patient, wherein the securement platform comprises a groove aligned with the longitudinal axis.

15. The catheter assembly of claim 14, wherein the groove extends through the securement platform.

16. A catheter assembly, comprising:
- a catheter adapter having a distal end, a proximal end, a lumen extending between the distal end and the proximal end, and a side port, wherein a central axis of a fluid path extending through the side port is disposed at an angle with respect to a longitudinal axis of the catheter adapter;
- a wedge disposed within the lumen of the catheter adapter; and
- a septum disposed within the lumen of the catheter adapter, wherein the septum comprises a guide portion to direct movement of an instrument as the instrument is advanced distally from the side port through the catheter adapter, wherein the guide portion comprises a smooth curve extending into the wedge.

17. A catheter assembly, comprising:
- a catheter adapter having a distal end, a proximal end, a lumen extending between the distal end and the proximal end, and a side port, wherein a central axis of a fluid path extending through the side port is disposed at an angle with respect to a longitudinal axis of the catheter adapter; and
- a wedge comprising a groove proximate a tunnel, wherein the groove forms a side opening in the wedge that is aligned with the side port fluid path such that a fluid may flow from the side port fluid path distally through the groove and into the tunnel.

* * * * *

UNITED STATES PATENT AND TRADEMARK OFFICE
CERTIFICATE OF CORRECTION

PATENT NO. : 11,406,810 B2  
APPLICATION NO. : 16/551345  
DATED : August 9, 2022  
INVENTOR(S) : Weston Harding et al.

Page 1 of 1

It is certified that error appears in the above-identified patent and that said Letters Patent is hereby corrected as shown below:

On the Title Page

Item (73) Please change the Assignee information from "Beeton, Dickinson and Company" to read "Becton, Dickinson and Company."

Signed and Sealed this
Twenty-seventh Day of August, 2024

Katherine Kelly Vidal
*Director of the United States Patent and Trademark Office*